United States Patent [19]

Imada et al.

[11] Patent Number: 4,871,667

[45] Date of Patent: Oct. 3, 1989

[54] PROCESS FOR PREPARING MUCONIC ACID

[75] Inventors: Yukio Imada, Tokyo; Nobuji Yoshikawa, Kanagawa; Sumiko Mizuno, Tokyo; Takashi Mikawa, Kanagawa, all of Japan

[73] Assignees: Agency of Industrial Science & Technology; Ministry of International Trade and Industry of Japan, both of Tokyo, Japan

[21] Appl. No.: 800,027

[22] Filed: Nov. 20, 1985

[30] Foreign Application Priority Data

Nov. 26, 1984 [JP] Japan .................................. 59-248205
Nov. 26, 1984 [JP] Japan .................................. 59-248207
Jul. 30, 1985 [JP] Japan .................................. 60-166902

[51] Int. Cl.$^4$ ........................... C12P 7/44; C12P 7/40
[52] U.S. Cl. .................................. 435/142; 435/830; 435/843; 435/840; 435/136
[58] Field of Search ............... 435/136, 142, 245, 253, 435/830, 843, 822

[56] References Cited

U.S. PATENT DOCUMENTS 3,816,255 6/1974 Tanno et al. .................... 435/840 X

OTHER PUBLICATIONS

Ruisinger et al., *Arch. Microbiol.*, vol. 110, pp. 253–256 (1976).
Bergey's Manual of Determinative Bacteriology, 8th Ed., 1979, pp. 599–601.
Sutherland et al., "Catabolism of Substituted Benzoic Acids by Streptomyces Species", *Appl. and Environ. Microbiol.*, 1981, pp. 442–448, vol. 41.

*Primary Examiner*—Charles F. Warren
*Assistant Examiner*—Irene Marx
*Attorney, Agent, or Firm*—Oblon, Spivak, McClelland, Maier & Neustadt

[57] ABSTRACT

Muconic acid is obtained from the culture of strains of Arthrobacter sp. mutant strains, strains belonging to Corynebacterium acetoacidophilum, Corynebacterium lilium, genus Brevibacterium or genus Microbacterium.

2 Claims, No Drawings

PROCESS FOR PREPARING MUCONIC ACID

FIELD OF THE INVENTION

This invention relates to a process for producing muconic acid.

BACKGROUND OF THE INVENTION

It is known to produce muconic acid from benzoic acid using mutant strains belonging to genus corynebacterium (Hakko Kogaku, Vol. 55, p. 95–97, 1977). Also a process using Arthrobacter sp. (DSM 20427) is known (Arch. Microboil. Vol. 110, p. 253–256).

We have extensively investigated processes for preparing muconic acid with improved productivity using benzoic acid as the carbon source, and we found microorganisms which are capable of converting benzoic acid to muconic acid at high yield. On the basis of this discovery, we completed this invention.

DISCLOSURE OF THE INVENTION

This invention provides a process for producing muconic acid comprising culturing a microorganism selected from: (i) Arthrobacter sp. T-8626 or mutant strains thereof which are capable of producing muconic acid; (ii) a microorganism which belongs to *Corynebacterium acetoacidophilum* or *Corynebacterium lilium* and is capable of producing muconic acid; and (iii) a microorganism which belongs to genus Brevibacterium or genus Microbacterium and is capable of producing muconic acid, using benzoic acid as the carbon source and obtaining muconic acid from the culture.

SPECIFIC DESCRIPTION OF THE INVENTION

The microorganisms used in this invention are selected from the following classes (i), (ii) and (iii).

(i) Microorganisms belonging to genus Arthrobacter and being capable of producing muconic acid such as Arthrobacter sp. T-8626 (Ferm (Fermentation Research Institute, Agency of Industrial Science and Technology, Ministry of International Trade and Industry, Japan, Bikoken)Deposition No. 7952) and its mutant strains, for instance Arthrobacter sp. T-8626-11 (FIRM Deposition No. 7953.)

Arthrobacter sp. T-8626 is a bacterium which was isolated from soil by us, and the bacteriological properties are as follows.

(a) Microscopic characteristics

Characteristics of the colony formed in the nutrient agar medium at 30° C. for 1 week.
1. Shape of colony: Round
2. Size: 2–4 mm
3. Upheaval of the surface: Convex
4. Appearance of the surface: Smooth
5. Gloss: Dull luster
6. Color: Initially greyish white, later yellowish
7. Transparency: Opaque
8. Periphery: Entire Morphological properties during culturing at 30° C. for 3–24 hours.
1. Cell morphology: Cells grow non-uniformly during the first 3 hours or so, becoming long rod-like and clavate. Later septa forms in the central part and cells bend at the septa and fission is repeated. Bending continues up to the 6–8th hour. After the 12th hour, almost all cells exhibit bacilliform, becoming diplococcal, and streptococcal and become uniform.
2. Polymorphism: Polymorphic. Cells change from rather a short filamentous state to a short rod and coccal state.
3. Mode of fission: Bending type
4. Motility: None
5. Spore formation: None
6. Grain reaction: Weakly positive for about 8 hours after the start of culturing, and negative after 12 hours
7. Acid-fastness: -

(b) Physiological properties
1. Growth under anaerobic condition: -
2. Growth under aerobic condition: +
3. Catalase: +
4. Oxidase: -
5. OF test: -
6. Reduction of nitrate: +
7. Hydrolysis of gelatin: ±
8. Hydrolysis of casein: -
9. Hydrolysis of starch: ±
10. Urease: +
11. Growth in 5% NaCl: +
12. Growth in 10% NaCl: -
13. Growth temperature range:
    4° C. -
    10° C. ±
    20° C. ++
    26° C. ++
    30° C. +++
    37° C. +++
    42° C. ±
14. Acid formation from carbohydrates: Indicated in Table 1
15. Assimilation of organic acids: Indicated in Table 2

(c) Biochemical properties
1. Composition of DNA bases: GC content 66.5%
2. Principal amino acid of cell wall: Lysine
3. Glycolate test: Acyl type
4. Type of peptidoglucan: The muramic acid residues of the peptidoglycan is of Lys-Ala type (d) Taxonomical properties: The present strain T-8626 is a Gram-negative bacterium which exhibits a coryneform in a period of the cell cycle, bending type fission, and a slightly branched polymorph. The GC content of the DNA thereof is as high as 70%. These facts suggest that this strain belongs to the family Corynebacteriaceae, Mycobacteriaceae or Nocardiaceae. Of these, Mycobacteriaceae and Nocardiaceae are characterized in that the principal amino acid of the cell wall is DL-diaminopimelic acid, and the muramic acid residues of the peptidoglycan exhibits a glycolyl type. On the other hand, Corynebacteriaceae has various compositions of cell wall amino acids and the principal amino acids of the cell wall are LL-diaminopimelic acid, lysine, ornithine, or diaminobutyric acid. The analysis of amino acids of cell wall and the muramic acid residue of the peptidoglycan has shown that in the present strain T-8626, the principal amino acid of the cell wall is lysine and the muramic acid residue of the peptidoglycan is acyl type. From these facts, it was revealed that the strain T-8626 belongs to coryne type bacteria group.

Identification of genus level

The genus and species of bacteria of coryneform bacteria are discriminated on the basis of unstable features and minute differences. Therefore, the classification and identification of these bacteria are difficult and often a subject of dispute. Yamada, Komagata, et al, conducted taxonomical study on coryneform bacteria and proposed a new taxonomical system for this group of bacteria (1969–1972). They took up amino acid composition of the cell wall, the GC content of the DNA, the assimilation pattern of carbohydrates and organic acids and modes of cell fission as classification factors of coryneform bacteria at the genus level and classified these bacteria into 7 genera—Corynebacterium, Brevibacterium, Arthrobacter, Curtobacterium, Cellulomonas, Pimelobacter and an unknown group.

The strain T-8626 is regarded to belong to the Arthrobacter from the facts that the strain does not produce acids from various carbohydrates, and it has lysine as the principal amino acid of the cell wall, and that the fission mode thereof is bending.

Identification at species level

In the genus Arthrobacter, 21 species have been reported up to now. These species are discriminated by way of the physiological and biochemical properties thereof. Especially, the amino acid compositions of the interpeptide bridges of the cell wall (peptidoglycan type) is regarded a very important characteristic for the identification thereof. (Refer to Schleifer & Kandler: Bacteriological Review, 36, 407–477 (1972); and the DSM Catalog, edited by Claus & Schaab-Engels, 2nd Ed. 1977.)

The strain T-8626 is considered to be a species very close to *Arthrobacter crystallopoietes* from the facts that the peptidoglycan type thereof is of Lys-Ala type. According to the original description of J. C. Ensign & S. C. Rittenberg (1963), the original reporters of *Arthrobacter crystallopoietes*, this species is characterized in that it produce crystals of a green pigment in the culture medium when it is cultured in a medium containing 2-hydroxypyridine as the sole carbon source.

Thus, a standard strain of *Arthrobacter crystallopoietes* JCM 2522, was obtained and compared with the present strain. When the standard strain of *Arthrobacter crystallopoietes* (JCM 2522) was cultured with a medium containing 2-hydroxypyridine as the sole carbon source, it produced crystals of a green pigment in the medium. In contrast, when the present strain was cultured with the same medium, the production of the green pigment was not detected. Further, several differences in the other physiological and biochemical properties were observed between the two strains.

Consequently, the present strain T-8626 is considered to be a new species of the genus Arthrobacter. However, the definite nomenclature of the species will be reported after many strains of related species are found. The strain T-8626 is designated simply as Arthrobacter sp. for the time being.

TABLE 1

Assimilation of various carbohydrates (production of acids)

| Arthrobacter | A. aurescens | A. citreus | A. globiformis | A. nicotianae (by Yamada and Komagata, 1972) | A. oxydans | A. pascens | A. ramosus | A. tumescens | A. urefaciens | Arthrobacter sp. (t-8626) | Arthrobacter sp. DSM 20407 | A. crystallopoietes JCM 2522 |
|---|---|---|---|---|---|---|---|---|---|---|---|---|
| Alabinose | — | — | — | — | — | — | — | — | — | — | — | — |
| Xylose | — | — | — | — | — | — | — | — | — | — | — | — |
| Rhamnose | — | — | — | — | — | — | — | — | — | — | — | — |
| Glucose | — | — | — | — | — | — | — | — | — | — | ± | — |
| Fructose | — | — | — | — | — | — | — | — | — | — | — | — |
| Mannose | — | — | — | — | — | — | — | — | — | — | — | — |
| Galactose | — | — | — | — | — | — | — | — | — | — | — | — |
| Solbose | — | — | — | — | — | — | — | — | — | — | — | — |
| Sucrose | — | — | — | — | — | — | — | — | — | — | — | — |
| Lactose | — | — | — | — | — | — | — | — | — | — | — | — |
| Maltose | — | — | — | — | — | — | — | — | — | — | — | — |
| Trehalose | — | — | — | — | — | — | — | — | — | — | — | — |
| Cellobiose | — | — | — | — | — | — | — | — | — | — | — | — |
| Raffinose | — | — | — | — | — | — | — | — | — | — | — | — |
| Dextrin | — | — | — | — | — | — | — | — | — | — | — | — |
| Starch | — | — | — | — | — | — | — | — | — | — | — | — |
| Inulin | — | — | — | — | — | — | — | — | — | — | — | — |
| Glycerol | — | — | — | — | ± | — | — | — | — | — | — | — |
| Erythritol | — | — | — | — | — | — | — | — | — | — | — | — |
| Adenitol | — | — | — | — | — | — | — | — | — | — | — | — |
| Mannitol | — | — | — | — | — | — | — | — | — | — | — | — |
| Dulcitol | — | — | — | — | — | — | — | — | — | — | — | — |
| Sorbitol | — | — | — | — | — | — | — | — | — | — | — | — |
| Inositol | — | — | — | — | — | — | — | — | — | — | — | — |
| Arbutin | — | — | — | — | — | — | — | — | — | — | — | — |
| Aesculin | — | — | — | — | — | — | — | — | — | — | — | — |
| Salicin | — | — | — | — | — | — | — | — | — | — | — | — |
| α-Methylglucoside | — | — | — | — | — | — | — | — | — | — | — | — |

TABLE 2
Assimilation of Organic Acids

| Arthrobacter | A. aurescens | A. citreus | A. globiformis | A. nicotianae (by Yamada and Komagata, 1972) | A. oxydans | A. pascens | A. ramosus | A. tumescens | A. urefaciens | Arthrobacter sp.(t-8626) | Arthrobacter sp. DSM 2047 | A. crystallopoietes JCM 2522 |
|---|---|---|---|---|---|---|---|---|---|---|---|---|
| Acetic acid | + | + | + | + | + | + | + | + | + | + | + | + |
| Pyruvic acid | + | + | + | + | + | + | + | + | + | + | + | + |
| Lactic acid | + | + | + | + | + | + | + | + | + | + | + | + |
| Malic acid | + | + | + | + | + | + | + | + | + | + | + | + |
| Succinic acid | + | + | + | + | + | + | + | + | + | + | + | + |
| Fumaric acid | + | + | + | + | + | + | + | + | + | + | + | + |
| α-Ketoglutaric acid | + | + | + | + | + | + | + | + | + | + | + | + |
| Citric acid | − | − | + | − | + | + | − | + | + | + | + | + |
| Formic acid | + | + | + | − | − | − | − | − | − | − | − | − |
| Propionic acid | + | + | + | + | + | + | + | + | + | + | + | + |
| Butyric acid | − | + | + | + | + | + | + | + | + | + | + | + |
| Oxalic acid | + | + | + | + | + | + | + | + | + | + | + | + |
| Malonic acid | − | − | − | − | − | − | − | − | − | − | − | − |
| Glutaric acid | − | − | + | + | + | + | + | ++ | + | + | ++ | ++ |
| Adipic acid | + | + | − | − | − | − | − | − | − | + | ++ | ++ |
| Pimelic acid | − | − | − | − | − | − | − | − | − | − | − | − |
| Glycolic acid | + | + | + | + | + | + | + | + | + | + | + | + |
| Glyoxylic acid | + | + | + | + | + | + | + | + | + | + | + | + |
| Gluconic acid | + | + | + | + | + | + | + | + | + | + | + | + |
| Hippuric acid | + | + | + | + | + | + | + | + | + | + | + | + |
| Uric acid | + | − | + | + | + | + | + | + | + | + | + | + |

TABLE 3

Comparison of physiological and biochemical properties of Arthrobacter sp. (T-8626) and A. crystallopoietes (JCM 2522)

| Properties | (T-8626) | (JCM 2522) |
|---|---|---|
| Gramm's stain | Weakly positive | Weakly positive |
| Mode of Fission | Bending | Bending |
| Motility | None | None |
| OF test | — | — |
| Reduction of nitrate | + | + |
| Hydrolysis of gelatin | + | + |
| Hydrolysis of casein | — | — |
| Hydrolysis of starch | ± | — |
| Urease | + | + |
| Growth in 5% NaCl | + | + |
| Growth in 10% NaCl | — | + |
| Growth temp. range | | |
| 4° C. | — | — |
| 10° C. | — | — |
| 20° C. | ++ | + |
| 26° C. | ++ | ++ |
| 30° C. | ++ | ++ |
| 37° C. | ++ | + |
| 42° C. | + | — |
| Assimilation of carbohydrates (formation of acids) | — | — |
| Assimilation of organic acids | + | + |
| Composition of DNA bases | 66.8% | 63.6% |
| Composition of cell wall | Lysine | Lysine |
| Peptidoglycan type | Lys—Ala type | Lys—Ala type |
| Glycolate test | Acyl type | Acyl type |
| Formation of pigment in 2-hydroxypyridine medium | — | + |

The mutant strain Arthrobacter sp. T-8626-11 was obtained by the procedure of Reference Example 1.

(ii) Microorganisms belonging to *Corynebacterium acetoacidophilum* and *Corynebacterium lilium* which are able to produce muconic acid, such as *Corynebacterium acetoacidophilum* ATCC 13870, *Corynebacterium lilium* ATCC 21793, etc.

(iii) Microorganisms belonging to genus Brevibacterium or genus Microbacterium which are able to produce muconic acid such as *Brevibacterium flavum* ATCC 13826, *Brevibacterium saccharolyticum* ATCC 14066, *Brevibacterium divaricatum* ATCC 21642, *Brevibacterium lactofermentum* ATCC 13655, *Microbacterium ammoniaphilum* ATCC 21645, ATCC 15354, etc.

The microorganisms used in the present invention are available from Ferm (Fermentation Research Institute, Agency of Industrial Science and Technology, Ministry of International Trade and Industry, Japan) and ATCC (American Type Culture Collection).

Culture media usable for the present invention are not specifically limited insofar as they contain benzoic acid as the carbon source.

In addition to benzoic acid, various carbohydrates, organic acids, etc. can be added. As the nitrogen source, organic ammonium salts, inorganic ammonium salts, urea, etc. can be used.

Further various inorganic substances such as various kinds of phosphoric acid salts, sulfate salts can be optionally used, and also various organic nutrient substances can be optionally added.

Culturing is carried out usually for 12 hours to 10 days under aerobic condition.

The pH of the culture medium is 4–10, and the temperature is in the range of 20°–40° C.

Either cells in the growth phase or cells in the resting phase can be used in the production of muconic acid.

Any conventional method generally used for collection and purification of organic substances can be employed for collection and purification of the muconic acid.

The obtained muconic acid can be converted to adipic acid by hydrogenation, and is useful as a starting material for 1,4-dicarboxylic acid derivatives and also useful as a raw material for functional resins.

Thus muconic acid can be obtained from benzoic acid at high yield.

EMBODIMENTS OF THE INVENTION

Now the invention will be illustrated by way of working examples. In the following examples, identification of substances was carried out by gas chromatography, mass spectrometry, et al in comparison with standard samples.

EXAMPLE 1

In 1 liter of water were dissolved 10 g of peptone, 5 g of yeast extract, 10 g of NaCl, and 5 g of sodium benzoate, and the pH of the resulting solution was adjusted to 7.0. Each 50 ml of the prepared medium was poured into 500 ml flasks and all the portions were sterilized at 120° C. for 10 minutes.

In the meantime, Arthrobacter sp. T-8626 was cultured in a benzoic acid-containing slant medium at 30° C. for 3 days, and one platinum loop unit of the cultured microorganism was inoculated into one of the above-mentioned flasks and was cultured at 30° C. under agitation by a reciprocal agitator at 112 r.p.m. for 2 days. From this seed culture, the microorganism was inoculated into one of the above-mentioned flasks containing 50 ml of the culture medium in which the sodium benzoate content was modified to 3% so that the microorganism content was 8%. The culturing was continued at 30° C. for 2–3 days under agitation by the reciprocal agitator at the above-mentioned rate. It was found that 50 mg of cis, cis-muconic acid was produced (1 g/l).

REFERENCE EXAMPLE 1

Arthrobacter sp. T-8626 at the logarithmic growth phase was collected from its nutrient broth culture medium which had been subjected to liquid agitation culturing and was washed with citric acid buffer solution (pH 7.0).

The collected microorganism was irradiated with UV rays by the conventional method. The irradiated microorganism was subjected to an intermediate culturing overnight in a nutrient broth medium. The thus cultured microorganism was subjected to replica plating from the master plate of a nutrient agar medium to media in which benzoic acid was contained as the sole carbon source. Thus non-growth mutant strains were detected and collected on the latter media.

With respect to the collected mutant strains, ability of converting benzoic acid to muconic acid was checked and 2 muconic acid producing mutant strains were found.

EXAMPLE 2

Forty-five (45) ml of nutrient broth medium was placed in a 500 ml Erlenmeyer flask which was sterilized at 120° C. for 20 minutes. To this culture medium, a muconic acid-accumulating strain, Arthrobacter sp. T-8626-11 strain, which was one of the mutant strains obtained in Reference Example 1 and was grown in a nutrient agar medium, was inoculated. Agitation liquid culturing was carried out at 30° C. for 24 hours. Thereafter 5 ml of a separately sterilized sodium benzoate solution (50 g/l) was added thereto, and culturing was continued under the same conditions.

The muconic acid content in the obtained culture medium was analyzed and it was found that 4.5 g of muconic acid per liter of the culture medium was contained. (Molar yield against benzoic acid was 91%.)

EXAMPLE 3

In 1 liter of water were dissolved 10 g of peptone, 5 g of yeast extract, 10 g of NaCl and 5 g of sodium benzoate, and the pH of the resulting solution was adjusted to 7.0. Each 50 ml of the thus prepared medium was poured into 500 ml flasks and all the portions were sterilized at 120° C. for 10 minutes.

In the meantime, *Corynebacterium acetoacidophilum* ATCC 21421 was cultured in a benzoic acid-containing slant medium at 30° C. for 3 days, and one platinum loop unit of the cultured microorganism was inoculated into one of the above-mentioned flasks and cultured at 30° C. under agitation by a reciprocal agitator at 112 r.p.m. for 2 days. From this seed culture, the microorganism was inoculated into one of the above-mentioned flasks containing 50 ml of the culture medium in which the benzoic acid content was modified to be 3% so that the microorganism content was 8%. The culturing was continued at 30° C. for 3 days under agitation by the reciprocal agitator at the above-mentioned rate. It was found that 125 mg of cis, cis-muconic acid was produced (2.5 g/l).

EXAMPLE 4

In 1 liter of water were dissolved 10 g of peptone, 5 g of yeast extract, 10 g of NaCl and 5 g of sodium benzoate, and the pH of the resulting solution was adjusted to 7.0. Each 50 ml of the prepared medium was poured into 500 ml flasks and all the portions were sterilized at 120° C. for 10 minutes.

In the meantime, *Corynebacterium lilium* ATCC 21793 was cultured in a benzoic acid-containing slant medium at 30° C. for 3 days, and one platinum loop unit of the cultured microorganism was inoculated into one of above-mentioned flasks and was cultured at 30° C. under agitation by a reciprocal agitator at 112 r.p.m. for 2 days. From this seed culture, the microorganism was inoculated into one of the above-mentioned flasks containing 50 ml of the culture medium in which the benzoic acid content was adjusted to 3%. The culturing was continued at 30° C. for 3 days under agitation by the reciprocal agitator at the above-mentioned rate. It was found that 70 mg of cis, cis-muconic acid was produced (1.4 g/l).

EXAMPLE 5

In 1 liter of water were dissolved 10 g of peptone, 5 g of yeast extract, 10 g of NaCl and 5 g of sodium benzoate, and the pH of the resulting solution was adjusted to 7.0. Each 50 ml of the prepared medium was poured into 500 ml flasks and all the portions were sterilized at 120° C. for 10 minutes.

In the meantime, *Brevibacterium flavum* ATCC 14067 was cultured in a benzoic acid-containing slant medium at 30° C. for 3 days, and one platinum loop unit of the cultured microorganism was inoculated into one of the above-mentioned flasks and was cultured at 30° C. under agitation by a reciprocal agitator at 112 r.p.m. for 2 days. From this seed culture, the microorganism was inoculated into one of the flasks containing 50 ml of the culture medium in which the sodium benzoate content was modified to be 3% so that the microorganism content was 8%. The culturing was continued at 30° C. for 3 days under agitation by the reciprocal agitator at the above-mentioned rate. It was found that 130 mg of cis, cis-muconic acid was produced (2.6 g/l).

EXAMPLE 6

In 1 liter of water were dissolved 10 g of peptone, 5 g of yeast extract, 10 g of NaCl and 5 g of sodium benzoate, and the pH of the resulting solution was adjusted to 7.0. Each 50 ml of the prepared medium was poured into 500 ml flasks and all the portions were sterilized at 120° C. for 10 minutes.

In the meantime, *Microbacterium ammoniaphilum* ATCC 15354 was cultured in a benzoic acid-containing slant medium at 30° C. for 3 days, and one platinum loop unit of the cultured microorganism was inoculated into one of the flasks and was cultured at 30° C. under agitation by a reciprocal agitator at 112 r.p.m. for 2 days. From this seed culture, the microorganism was inoculated into one of the flasks containing 50 ml of the culture medium in which the sodium benzoate content was modified to be 3% so that the microorganism was 8%. The culturing was continued at 30° C. for 4 days under agitation by the reciprocal agitator at the above-mentioned rate. It was found that 120 mg of cis, cis-muconic acid was produced (2.5 g/l).

We claim:

1. A process for producing muconic acid, which comprises:
culturing a microorganism selected from the group consisting of:
(i)
Arthrobacter sp. T-8626, FERMBP-1035,
Arthrobacter sp. T-8626-11, FERMBP-1036
(ii)
*Corynebacterium acetoacidophilum* ATCC 21421,
*Corynebacterium acetoacidophilum* ATCC 13870,
(iii)
*Brevibacterium flavum* ATCC 13826,
*Brevibacterium saccharolyticum* ATCC 14066,
*Brevibacterium divaricatum* ATCC 21642,
*Brevibacterium lactofermentum* ATCC 13655,
*Microbacterium ammoniaphilum* ATCC 21645 and ATCC 15354,
wherein said culturing is carried out in the presence of benzoic acid as the carbon source, and
obtaining muconic acid from the culture.

2. The process for producing muconic acid recited in claim 1, wherein the culturing is carried out at a temperature in the range of 20°–40° C. and at a pH of the range of 4–10 in a culture medium containing benzoic acid or benzoate.

* * * * *